(12) United States Patent
Duckett et al.

(10) Patent No.: US 8,154,284 B2
(45) Date of Patent: Apr. 10, 2012

(54) HYPERPOLARITZATION OF COMPOUNDS FOR NMR, IN PARTICULAR BY MEANS OF PHIP

(75) Inventors: Simon Benedict Duckett, Heslington/York (GB); Gary George Green, Benton (GB); Paul Ian Elliott, Headingley/Leeds (GB); Joaquin Lopez-Serrano, Seville (ES)

(73) Assignee: University of York, Heslington, York (GB)

( * ) Notice: Subject to any disclaimer, the term of this patent is extended or adjusted under 35 U.S.C. 154(b) by 222 days.

(21) Appl. No.: 12/452,113

(22) PCT Filed: Jun. 17, 2008

(86) PCT No.: PCT/EP2008/004865
§ 371 (c)(1),
(2), (4) Date: Apr. 12, 2010

(87) PCT Pub. No.: WO2008/155093
PCT Pub. Date: Dec. 24, 2008

(65) Prior Publication Data
US 2010/0219826 A1 Sep. 2, 2010

(30) Foreign Application Priority Data
Jun. 18, 2007 (GB) .................................. 0711624.7

(51) Int. Cl.
*G01V 3/00* (2006.01)
(52) U.S. Cl. ........................................ 324/309; 324/300
(58) Field of Classification Search .......... 324/300–322; 600/407–445
See application file for complete search history.

(56) References Cited

U.S. PATENT DOCUMENTS

| 6,278,893 | B1 | 8/2001 | Ardenkjaer-Larson | |
| 6,574,496 | B1 * | 6/2003 | Golman et al. | ............... 600/420 |
| 7,495,435 | B2 * | 2/2009 | Appelt et al. | ................ 324/300 |
| 2002/0137965 | A1 | 9/2002 | Axelsson | |
| 2011/0285396 | A1 * | 11/2011 | Hofmann et al. | ............. 324/307 |

FOREIGN PATENT DOCUMENTS

| WO | WO 99/24080 | 5/1999 |
| WO | WO 2004/001995 | 12/2003 |
| WO | WO 2007/044867 | 4/2007 |

OTHER PUBLICATIONS

Maurice Goldman et al., "Hyperpolarization of $^{13}C$ through order transfer from parahydrogen: A new contrast agent for MRI", Magnetic Resonance Imaging 23 (2005) 153-157.

(Continued)

*Primary Examiner* — Brij Shrivastav
(74) *Attorney, Agent, or Firm* — Paul Vincent

(57) ABSTRACT

An NMR method is presented having enhanced sensitivity on a compound comprising hyperpolarizable nuclei, in particular applying enhanced PHIP. Polarization is thereby transferred from a prepared fluid, which is enriched with symmetric molecules of a particular spin state (e.g. para-hydrogen enriched), directly to the hyperpolarizable nuclei of a compound, without altering the chemical identity of the compound in this process. Spin transfer is achieved using a template having sites of ordered environment, and the fluid and the compound are brought together in the presence of the template. Polarization transfer to the hyperpolarizable nuclei of the compound is thereby easier to perform and can be applied to a broader scope of compounds.

15 Claims, 10 Drawing Sheets

OTHER PUBLICATIONS

Marten Ahlquist et al., "Rhodium(I) hydrogenation in water: Kinetic studies and the detection of an intermediate using $^{13}C\{^1H\}$ PHIP NMR spectroscopy", Inorganica Chimica Acta 360 (2007) 1621-1627.

Bouchard L-S at al., "Para-Hydrogen-Enhanced Hyperpolarized Gas-Phase Magnetic Resonance Imaging", 2007 Wiley-Vch Verlag, DE, vol. 46, No. 22.

Grant A.K. at al., "Early Experience with simple Methods for Parahydrogen-Induced Hyperpolarization", Proceedings of the ISMRM, 14TH Scientific Meeting, May 6, 2006.

Bargon J. et al., "Parahydrogen-Induced Hyperpolarization of 15N", Proceedings of the Joint Annual Meeting ISMRM-ESMRMB, 2007, May 19, 2007, p. 1317.

Blazina D. et al., "Applications of the parahydrogen phenomenon in inorganic chemistry", Dalton Transactions 20040907 Royal Society of Chemistry GB, No. 17, Sep. 7, 2004, pp. 2601-2609.

Jonischkeit, Thorsten et al., "Generating long-lasting $^1H$ and $^{13}C$ hyperpolarization in small moleecules with parahydrogen-induced polarization", The Journal of Chemical Physics 124, 201109 (2006).

Aime, Silvio, et al., "Polarization transfer from para-hydrogen to heteronuclei: Effect of H/D substitution. The case of AA'X and $A_2A'_2X$ spin systems", Journal of Magnetic Resonance 178 (2006) 184-192.

Aime, Silvio et al., "Hyperpolarization transfer from parahydrogen to deuterium via carbon-13", Journal of Chemical Physics, vol. 119, No. 17, 1. Nov. 2003.

Natterer, Johannes et al., "Parahydrogen induced polarization", Progress in Nuclear Magnetic Resonance Spectroscopy 31, (1997) 293-315.

* cited by examiner free pyridine

HYPERPOLARITZATION OF COMPOUNDS FOR NMR, IN PARTICULAR BY MEANS OF PHIP

This application is the national stage of PCT/EP2008/004865 filed on Jun. 17, 2008 and also claims Paris Convention priority to GB 0711624.7 filed Jun. 18, 2007.

BACKGROUND OF THE INVENTION

This invention relates to nuclear magnetic resonance (NMR) and magnetic resonance imaging (MRI). In particular, the invention relates to processes, devices and compounds for hyperpolarizing nuclei, and more specifically, to a method for carrying out an NMR experiment with enhanced sensitivity on a compound comprising hyperpolarizable nuclei.

NMR and MRI involve the detection of the transitions of nuclear spins between an excited state and a ground state in an applied magnetic field. Because the energy difference between these states is often small, the usual Boltzmann distribution of chemically identical nuclei is such that at room temperature the populations of nuclear spin states which are in dynamic equilibrium are almost identical. Since the strength of the detected signal in magnetic resonance experiments is proportional to the population difference, NMR signals are typically weak.

The strength of detectable NMR signals can however be enhanced by hyperpolarizing the magnetic nuclei. Hyperpolarization (also known as pre-polarization) in this context refers to a process in which a significant excess of magnetic nuclei are induced into the same spin state. This results in a large increase in available signal due to the much larger inequality of populations across the energy levels. In order for a hyperpolarized state to be useful, it is important that the spin state is sufficiently long lived to provide useful information, i.e. that the relaxation time of the spin state is 'long'. The rules governing the relaxation rates of nuclear spins are complex but known. It suffices to say that certain nuclei and spins systems have relaxation times which may extend to hours, days, months or even years.

There are a number of ways to induce certain nuclei into a hyperpolarized state. The simplest way is to cool the material to very low temperatures in the presence of a magnetic field, which will favour population of the lower energy state in which the spins of the nuclei are aligned with the applied magnetic field. This method is suitable for the production of hyperpolarized monatomic gases such as xenon or helium-3. The polarization levels of these nuclei have also been increased via the use of laser-based technologies.

One molecule that can be readily polarized is dihydrogen. Dihydrogen exists in various spin states, in which the spins of the individual nuclei are either aligned (ortho, the higher energy state), or opposed (para, the lower energy spin state). Para-hydrogen (p-$H_2$) is a nuclear spin isomer of dihydrogen with the spin configuration $\alpha\beta-\beta\alpha$. Para-hydrogen has no net magnetic moment and is therefore unobservable in this form by magnetic resonance methods. The ortho forms however retain magnetic resonance activity. The binuclear spin system of dihydrogen can be hyperpolarized simply by cooling to low temperature in the presence of a suitable catalyst which promotes conversion to the lower energy para-hydrogen state. In this process, the role of the catalyst is to perturb the dihydrogen molecule and thereby reduce its symmetry; otherwise a quantum mechanical selection rule prevents interconversion between the two spin states. Once separated from the catalyst and returned to room temperature, the para-hydrogen spin state may last for over a year in the absence of external effects.

Nuclei can be hyperpolarized by a process known as para-hydrogen induced polarization (PHIP). PHIP has proved to be highly efficient and has currently achieved greater enhancement of heteronuclei NMR signals than other methods known in the art. PHIP is generally the result of a chemical reaction in which the para-hydrogen nuclei are transferred into another molecule having certain symmetry properties. Under the right circumstances, the spin state of the para-hydrogen molecule is preserved in the spins of the two hydrogen atoms which become part of the new molecule. If other NMR-active nuclei are within coupling distance of the hydrogen nuclei, spin polarization of those nuclei can be transferred spontaneously. In this way, the signals of heteronuclei such as $^{13}C$, $^{15}N$ and $^{31}P$ can be enhanced. By way of example, WO 99/24080 describes a PHIP process in which para-hydrogen is added across a symmetrical carbon-carbon double bond containing a $^{13}C$ centre. In one example of such a process, Wilkinson's catalyst is first reduced by addition of para-hydrogen, followed by addition of an ethylene ligand. The resulting hydride ligands then undergo a migratory insertion reaction with the ethylene ligand, which subsequently dissociates from the complex to form uncoordinated hyperpolarized ethane. An overview of PHIP is given in Blazina et al, Dalton Trans., 2004, 2601-2609.

Conventional PHIP processes involve the chemical addition of para-hydrogen to hydrogenatable substrates (compounds), usually organic substrates (compounds) containing double and triple bonds. This processes are therefore limited to substrates (compounds) capable of undergoing dihydrogenation. Furthermore, hydrogen equivalence is not preserved at all stages, which leads to some loss of hyperpolarization through relaxation.

It is the object of the invention to present a method for carrying out an NMR experiment on a compound comprising hyperpolarizable nuclei, wherein polarization is transferred to the hyperpolarizable nuclei of the compound, which is easier to perform and which can be applied to a broader scope of compounds, in particular compounds that may not undergo a hydrogenation reaction.

SUMMARY OF THE INVENTION

This object is achieved, in accordance with the invention, by a method for carrying out an NMR experiment with enhanced sensitivity on a compound comprising hyperpolarizable nuclei, with the steps of:
a) preparing a fluid having a temperature TF, containing spatially symmetric molecules comprising two halves each, with a non-Boltzmann nuclear spin state distribution of the symmetric molecules at this temperature TF,
b) providing a compound with a defined chemical identity,
c) providing a template that offers sites of ordered environment for the two halves of a symmetric molecule and a compound which can be arranged at each site,
wherein the ordered environment distinguishes chemically or magnetically the two halves of a symmetric molecule arranged at each site,
and wherein the ordered environment allows interaction via scalar coupling or dipolar coupling between the two halves of a symmetric molecule and a compound arranged at each site,
d) bringing together the prepared fluid, the provided compound and the provided template, thereby transferring the spin order from the symmetric molecules to the hyperpolarizable nuclei of the compound during a temporary association of the symmetric molecules, the compound, and the template while ultimately keeping the chemical identity of the compound, and e) performing an NMR measurement on the compound comprising hyperpolarized nuclei prepared in step d).

As the core of the present invention, polarization is transferred from the prepared fluid, which is enriched with symmetric molecules of a particular spin state (e.g. para-hydrogen enriched), directly to the hyperpolarizable nuclei of a compound, without altering the chemical identity of the compound in this process. To achieve this spin transfer, the invention proposes to use a template having sites of ordered environment, and the fluid and the compound are brought together in the presence of the template.

Such a site of ordered environment acts as a broker between a symmetric molecule (or its two halves) and a compound. A site of ordered environment first of all allows an arrangement of both a symmetric molecule and a compound at the site, i.e. it allows a bonding of some kind of a symmetric molecule and a compound to the site. Typically, the bonding is rather loose, and may be of coordinative type.

When a symmetric molecule is (or its two halves are) attached to a site of ordered environment, the two halves of the symmetric molecule become chemically or magnetically distinguishable; in other words the symmetry of the symmetric molecule is broken. This is a characteristic of the site of ordered environment according to the invention. In this situation, entropy will try to bring the nuclear spins of the two halves of the symmetric molecule closer to the thermal equilibrium; however the polarization of the symmetric molecule will need a destination to go to. As a consequence, the polarization of the symmetric molecule becomes—in principle—available for a transfer.

Further, when both a symmetric molecule (or its two halves) and a compound are arranged at a site of ordered environment, the site of ordered environment mediates (establishes) a coupling of the nuclear spins of the halves of the symmetric molecule and the compound (or its hyperpolarizable nuclei); this is another characteristic of the site of ordered environment according to the invention. The coupling mechanism may, in particular, be scalar coupling or dipolar coupling. By mediating the coupling, the compound becomes a possible destination of polarization to be transferred from the symmetric molecule. Typically, the site of ordered environment causes a close spatial neighbourhood of the spin-carrying atoms of the symmetric molecule and the hyperpolarizable nuclei of the compound on an atomic scale.

Basically by bringing together the prepared fluid, the provided compound and the template, and inducing an (at least) temporary association of the symmetric molecules, the compound and the template, the spin order transfer can be performed in a rather quick and simple way. In the most simple case, the fluid, the compound and the template can be mixed in solution, or a mixture of two components (such as the fluid and the compound) flows over or through the third component (typically the template). Under the conditions of the inventive method, the spin order transfer occurs in principle automatically, without a necessity for applying further measures. However, in accordance with the invention, the spin order transfer can be accelerated or intensified by some measures as described further below.

There is no net chemical reaction necessary between the symmetric molecules and the compound to be polarized in order to achieve the inventive spin order transfer, what makes the spin order transfer inherently simple. The chemical identity of the compound before and after the spin order transfer is the same, in accordance with the invention. For lack of the need for a chemical reaction, the inventive method becomes available for in principle every compound, in particular also compounds without double or triple C—C bonds necessary for conventional PHIP. Further, as compared to conventional PHIP, non-reactive symmetric molecules such as $(^{15}N)_2$ become available as a source of hyperpolarization.

In accordance with the invention, the ordered environment may take the form of a homogeneous or heterogeneous polarization transfer catalyst. For example, the heterogeneous system may comprise a supported transition metal centre, a microscopic channel within a material such as a zeolite, a nanotube, or a nanoparticle, a solvent with liquid crystalline properties, or any other feature that induces a short range magnetic differential with respect to the otherwise symmetric molecule and compound to be polarized.

In accordance with the invention, the compound is typically a molecule, but may be also an ion, a polymer, a nanoparticle, a supermolecular assembly, a peptide, a protein, or something else with a chemical identity. The chemical identity is defined by a chemical formula and a chemical (spatial) structure. Note that TF—i.e. the temperature at which the symmetric molecules have their non-equilibrium spin distribution as defined in step a)—is typically the temperature at which the spin transfer of inventive step d) takes place. The non-equilibrium spin distribution of the symmetric molecules, which is still present when starting the spin order transfer of step d) in accordance with the invention, drives the spin order transfer.

Further below, examples are given for combinations of symmetric molecules, compounds and templates with sites of ordered environment. It should be mentioned that for a particular combination of symmetric molecules (as spin order source) and compound (as spin order destination, for the purpose of performing an NMR experiment on the hyperpolarized compound), a specific template must be chosen in order to accomplish the inventive method.

In a highly preferred variant of the inventive method, the symmetric molecules comprise para-hydrogen. Transferring spin order from para-hydrogen (p-$H_2$) to a compound in accordance with the invention is also referred to as "enhanced PHIP" here. Para-hydrogen is relatively inexpensive to prepare and can easily be arranged at different types of templates, and therefore is of great importance in practice. Typically p-$H_2$ is prepared as a fluid (liquid or gas) of p-$H_2$ enriched $H_2$. In alternative to p-$H_2$, the symmetric molecule can be a derivative of para-hydrogen with two hydrogen ligands whose nuclei are hyperpolarized. Further alternatives for symmetric molecules include e.g. $D_2$, $(^{15}N)_2$, oxalic acid, oxalate (HOOCCOOH), and cis-1,2-diphenyl ethene.

In another highly preferred variant, the sites of ordered environment each comprise a metal complex, in particular a transition metal complex. Typical transition metal atoms for the invention include Ru, Rh, Ir, W, Pd or Pt. Metal complexes, and in particular transition metal complexes, allow the attachment of numerous different symmetric molecules and compounds, in particular by coordinative bonding, and are therefore very important in practice.

In a further variant of the inventive method, the template comprises a zeolite. Zeolites are in particular useful for a continuous preparation of hyperpolarized compound. For example, a zeolite, binding p-$H_2$, can be placed in a cell, with a flow of a solution of the compound over or through the zeolite. The suitability of zeolites for a spin order transfer from p-$H_2$ has been shown in experiment. Also note that zeolites may store fluid and/or compound in its cavities, what may be of use for the inventive method.

In an advantageous variant, the hyperpolarizable nuclei of the compound include H, D, $^{29}$Si, $^{13}$C, $^{15}$N, $^{31}$P and/or $^{19}$F. D indicates deuterium (2H). Examples for spin order transfer in accordance to the invention with to above mentioned nuclei are detailed below. These nuclei are of particular importance in practice. Note that per compound (which is typically a molecule), there may be one hyperpolarizable nucleus or a plurality of hyperpolarizable nuclei.

In a further preferred variant of the inventive method, the compound is a metabolite. More generally, in accordance with the invention, the compound may be a substance to be found in or applicable to the human or animal body, in particular including drugs and prodrugs. This is particularly advantageous in medical applications.

An advantageous variant of the inventive method is characterized in that the compound comprises an electron donor for attaching to a site of ordered environment, in particular wherein the electron donor is N, NH, S, P or O. The electron donor typically has one or more pairs of electrons, which can help establishing an interaction to a site of ordered environment, in particular by means of a coordinative bonding. Note that the compound comprises typically more atoms than those of the electron donor. For example, P may be hyperpolarized in phosphine, and O in $CO_2$, as shown in experiments.

In a further variant, the compound is a gas, in particular ($^{13}$C)$O_2$. Inventive polarization transfer to $CO_2$ has been shown in experiment. Another compound in gaseous form may be ($^{15}$N)$_2$, in particular for inhalation by a patient.

In a highly preferred variant of the inventive method, at the end of step d), the compound comprising hyperpolarized nuclei is separated from the site of ordered environment. This variant is particularly useful when the template would disturb or prohibit the NMR experiment on the compound, e.g. if the template degrades the NMR signal, or the template is toxic and the compound is to be inserted into a living human or animal body for an imaging experiment. If necessary, the separation can be enhanced by dedicated measures, in particular physical measures (e.g. dynamic pressure) or chemical measures (such as a pH alteration). It should be mentioned here that the spin order transfer, in accordance with the invention, can be established in a continuous flow experiment, such that at the same time some compound is in inventive step b), while some compound is in inventive step d), and some compound has already finished step d) and has been separated from the template.

In a highly preferred variant of the inventive method, in step d) the spin order is transferred spontaneously. In other words, the spin order is transferred from the symmetric molecules to the compound without applying an RF (=radio frequency) pulse sequence. This simplifies the spin order transfer enormously, since it can be performed outside of an NMR coil arrangement. Alternatively, an RF pulse sequence may be applied for supporting the spin order transfer from the symmetric molecule to the compound. In the latter case, in accordance with the invention, there is typically a low (i.e. non-zero, but for typical NMR experiments unsatisfactory) spontaneous spin order transfer which is increased by the application of the RF pulse sequence then. Note that the spin order transfer can be predominantly or completely induced (caused) by an RF pulse sequence, though (i.e. in the latter case without applying the RF pulse sequence, no polarization transfer would be observed). However, in accordance with the invention, it is highly preferred that at least some (and preferably all) of the spin order transfer is obtained without the application of an RF pulse sequence.

In another highly preferred variant, during step d), the entirety of the prepared fluid, the provided compound and the provided template brought together is shaken. Applying a fluid flow or fluid shear, in particular induced by shaking, in the entirety has been found to enhance spin order transfer; it is assumed that the exchange of symmetric molecules having transferred their spin polarization already, and/or the exchange of compound having received nuclear spin polarization, can be accelerated at the template in this way. Typical shaking of an NMR sample tube, which has led to an efficient spin order transfer in experiment, is a few seconds with a frequency of about 5 Hz, resulting in about 20 forth and back movements with an amplitude of several centimetres. Note that shaking can be done manually if desired. Alternatively, a machine-induced oscillation or vibration or a sonic or ultrasonic treatment may be applied. Further, bubbling a gas through a liquid may induce a beneficial fluid flow or shear in accordance with the invention.

In a further development of the above variant, during shaking the entirety is exposed to a magnetic field, preferably wherein the field strength is 1 T or less, most preferably wherein the field strength is between 20 µT and 0.1 T. Experiments have shown that a relative movement of the entirety and a magnetic field can enhance the spin order transfer. Such a relative movement can be established by shaking the entirety in a magnetic field. For shaking, the magnetic field is typically static, and earth magnetic field is enough for good transfer efficiency. The magnetic field in this further development may be inhomogeneous in accordance with the invention. In accordance with the invention, the magnetic field conditions during step d) can be used to influence or even control the spin order transfer, in particular the phase of the final, enhanced NMR-signal.

Moreover, in a further preferred variant of the inventive method, during step d), the entirety of the prepared fluid, the provided compound and the provided template brought together is exposed to an oscillating magnetic field, in particular wherein the amplitude of the field strength of the oscillating magnetic field is between 20 µT and 0.1 T. By altering the magnetic field, a relative movement of the entirety and the magnetic field can be established with a stationery entirety. In experiment, manually moving a hand-held permanent magnet several times back and forth near an NMR tube (i.e. near the entirety) has resulted in good spin order transfer. The oscillating magnetic field may be inhomogeneous across the entirety (NMR sample tube), in accordance with the invention. Note that a typical oscillation frequency in accordance with the invention is about 1 to 10 Hz.

Further, in an advantageous variant of the inventive method, the chemical identity of the compound as prepared in step b) is the same as the chemical identity of the compound as subject to the NMR measurement of step e). This variant is particularly simple. Alternatively, in accordance with the invention, between steps d) and e) the compound may undergo a chemical reaction; however this chemical reaction is independent of the spin order transfer of step d).

Also within the scope of the present invention is the use of the inventive method or one of its variants in an NMR imaging experiment, in particular wherein the compound is used as a contrast agent. The hyperpolarized nuclei of the compound may be used for image formation. The invention can, in particular, be used to obtain images of a living human or animal body or parts of it, in order to prepare medical diagnostics or therapy. Typically, the compound is applied to the human or animal body after having undergone inventive step d).

Further advantages can be extracted from the description and the enclosed drawing. The features mentioned above and below can be used in accordance with the invention either

DESCRIPTION OF THE PREFERRED EMBODIMENT

Figure 1:
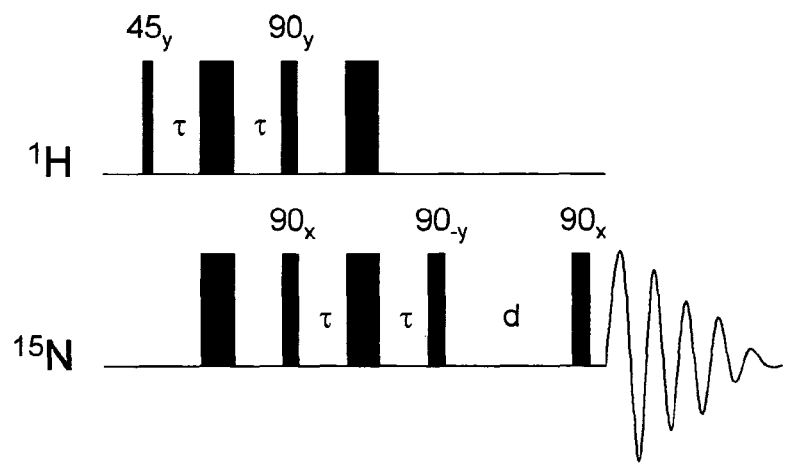
FIG. 1 shows a PH-INEPT+EXSY pulse sequence; pulses shown are $180_x°$ unless otherwise stated.

In the following, experimental descriptions and results are presented for experiments applying the principles of the inventive method.

EXAMPLE 1

Preparation of Hydride Complexes $Ir(H)_2(PPh_3)_2(pyridine)_2^+$ was generated by bubbling $H_2$ through a solution of $[Ir(COD)(PPh_3)_2]^+$ (COD=cycloocta-1,5-diene) in dichloromethane in the presence of excess pyridine and isolated in the solid state as has been previously described by Rosales et al (*Dalton Trans.*, 2004, 2952) When the same reaction was carried out using $^{15}N$-labelled pyridine under p-$H_2$, the hydride resonances of both $Ir(H)_2(PPh_3)_2$(pyridine)$_2^+$ and $Ir(H)_2(PPh_3)(pyridine)_3^+$ were substantially enhanced. This is attributable to the second order spin system that is generated when the hydride ligands become magnetically inequivalent.

The size of the enhanced hydride resonance of $Ir(H)_2$(PPh_3)(pyridine)$_3^+$ was much larger than that of $Ir(H)_2$(PPh_3)_2 (pyridine)$_2^+$ in contrast to their relative intensities when using $^{14}N$-pyridine. This suggests that the latter complex exchanges p-$H_2$ at a greater rate.

Analogues of these species were generated for $[Ir(COD)((P\{p\text{-tolyl}\}_3)_2]^+$ and $[Ir(COD)((P\{C_6H_4\text{-p-OMe}\}_3)_2]^+$. When the hydrogenation was carried out in the presence of $^{15}N$-pyridine using equimolar solutions of these complexes, similar hydride signals were observed to those generated using the $PPh_3$ system. When the signal to noise ratio of the hydride ligands of the product dihydride complexes was monitored, it was observed that the signals reduce in intensity the trend $PPh_3 > P\{p\text{-tolyl}\}_3 > P\{C_6H_4\text{-p-OMe}\}$ which suggests that the increased basicity of the phosphine leads to a reduction in the catalytic rate and hence reduction in the recycling of para-hydrogen nuclei into these hydride positions.

EXAMPLE 2

Polarization Transfer to $^{15}N$

A series of heteronuclear polarization experiments were utilised in order to transfer the enhanced polarization from hydride resonances to the $^{15}N$ of pyridine using PHIP adapted INEPT and INADAQUATE experiments (Haake et al, *J. Am. Chem. Soc.*, 1996, 118, 8688). These experiments included PH-INEPT, refocused PH-INEPT$^+$, INEPT(+π/4) and PH-INADAQUATE experiments. When recorded under identical conditions and with the signal to noise of the experiments normalised with respect to the relative signal strength of hydride resonances in $^1H$ spectra recorded immediately before each experiment, it was shown that the most efficient polarization transfer was achieved using the PH-INEPT experiment. The refocused version of this experiment only afforded about a third of the $^{15}N$ signal intensity, most likely due to transverse relaxation of the $^{15}N$ signal during the refocusing echo. The INEPT(+π/4) and PH-INADAQUATE experiments were found to be the least effective.

p-$H_2$ derived polarization was transferred from hydride ligands to the $^{15}N$ of pyridine in the complex $Ir(H)_2(pyridine)$(PPh_3)_2Cl$. The experiment described above was used as a preparative sequence in an EXSY type experiment. Here, a refocused sequence was necessary to generate observable in-phase $^{15}$N signals and hence the PH-INEPT+ sequence was used as a preparative block for a new PH-INEPT+ EXSY experiment. This preparative sequence was followed by a 90°$_{-y}$ pulse to store the $^{15}$N polarization as +z-magnetisation, a delay for ligand dissociation and then a further 90° read pulse. The signal for free $^{15}$N-pyridine was found to be enhanced by such an approach.

When tricyclohexylphosphine (PCy$_3$) ligands were used in place of PPh$_3$ ligands, the exchange rate of both H$_2$ and pyridine was substantially enhanced. Under these conditions, the $^1$H NMR spectra of the associated samples using either labelled or non-labelled pyridine contained large emission signals in the aromatic region of the spectrum at 7.43, 7.84 and 8.54 ppm due to the free substrate. These signals were most readily observed immediately after shaking the NMR tube in low field and then placing it in the spectrometer. This suggests that (i) under low field conditions there is spontaneous transfer of the PHIP effect to the protons of pyridine when the pyridine ligand is temporarily ligated to the iridium hydride complex; and (ii) exchange of ligated and free pyridine leads to the polarization of a portion of the free pyridine without having protons derived from p-H$_2$ chemically incorporated into the molecule. When 4-methylpyridine or purine was used in place of pyridine, related enhancements effects were also observed. Under these conditions, when $^{15}$N labelled pyridine was employed, substantial enhancement of the free pyridine $^{15}$N signal was also evident.

In a further experiment, a sample of [Ir(COD)(PCy$_3$)(py)]BF$_4$ (COD=cycloocta-1,5-diene, Cy=cyclohexyl, py=pyridine) was dissolved in methanol-d$_4$ at 300 K in an NMR tube. Excess pyridine (1-10 µL) was then added and the NMR tube pressurised with para-H$_2$. When the resultant reaction was monitored by $^1$H NMR spectroscopy, the appearance of emission signals of substantial intensity in the organic region of the spectrum between δ8 and δ6 was observed. The strongest of these peaks was observed at δ7.84 and 8.54 along with an enhanced signal that is in absorption at δ7.43. These peaks are coincident with those of free pyridine. The peaks were only observable with these enhanced characteristics when the observation process was started immediately after shaking the NMR tube outside the magnet and introducing it into the NMR spectrometer. Furthermore, the signals decayed over the course of a few successive scans when the magnetisation was read and partially destroyed using a hard +45° excitation pulse. The resonances of free pyridine were therefore observed to have been hyperpolarized.

In a similar manner, the following ligands were also hyperpolarized: 4-methylpyridine, 3-methylpyridine, nicotinamide, nicotine, pyridazine, purine, quinoline, quinazoline, quinoxaline and quinine.

This Example demonstrates that the reversible binding of a substrate and para-hydrogen can be utilised to hyperpolarize a substrate without the need to chemically incorporate nuclei from parahydrogen with the molecule. Thus no overall chemical reaction is required in contrast with previous studies.

Example 3 and 4 illustrate further procedures for obtaining and polarising transition metal complexes.

EXAMPLE 3

Radio Frequency-Assisted Polarisation Transfer 1 mg of hydrogenatable complex was dissolved in 500 µL of d$_4$-methanol in an NMR tube fitted with a Young's tap top. Approximately 1 mg of the substrate to be polarised (and 1 to 104 of a sacrificial hydrogen acceptor such as 1-phenylprop-1-yne is added if necessary). The sample was then degassed and pressurised by 3 to 3.5 bar of p-H$_2$. The tube was then shaken to dissolve the gas and transferred into the NMR spectrometer. NMR spectra were then recorded using the PH-INEPT+EXSY sequence (see FIG. 1) over a range of reaction delay times that varied between 50 ms and >1 s (see FIG. 3). PH-INEPT and PH-INEPT+ spectra were also recorded to give control spectra correlating to reaction time t=0 s (see FIG. 2).

Figure 2:
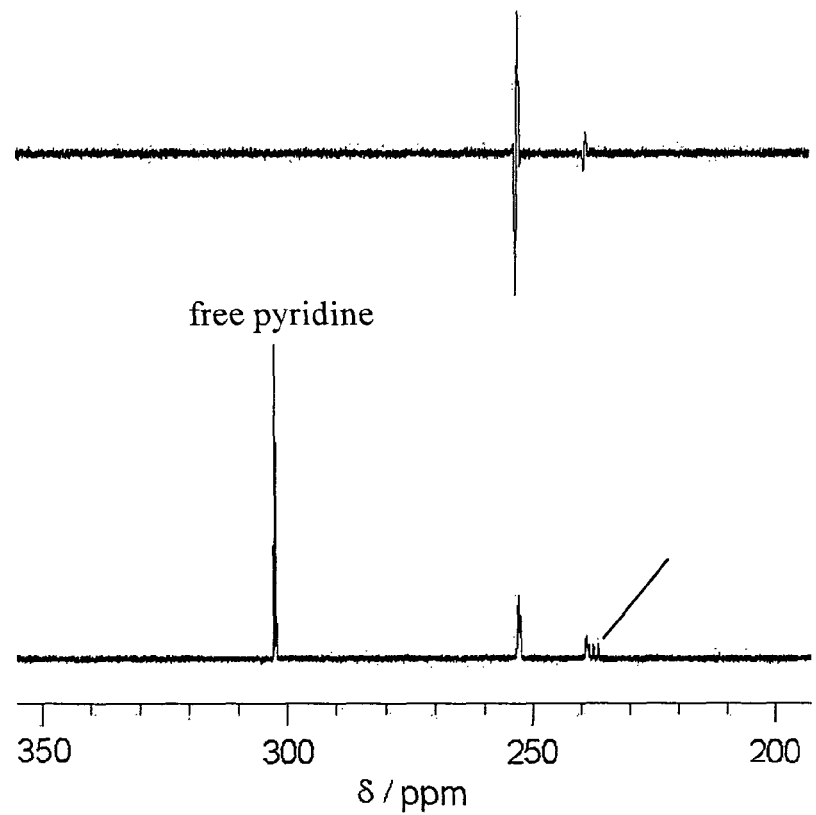
FIG. 2 shows (top) a PH-INEPT spectrum of a sample using $[Ir(COD)(P\{p\text{-tolyl}\}_3)_2]BF_4$ and $^{15}N$-pyridine showing signals for $[Ir(P\{p\text{-tolyl}\}_3)(H)_2(py)_3]^+$ (major) $[Ir(P\{p\text{-tolyl}\}_3)_2(H)_2(py)_2]^+$ (minor), (bottom) PH-INEPT+EXSY spectrum of the same sample with 500 ms reaction delay.
Figure 3:
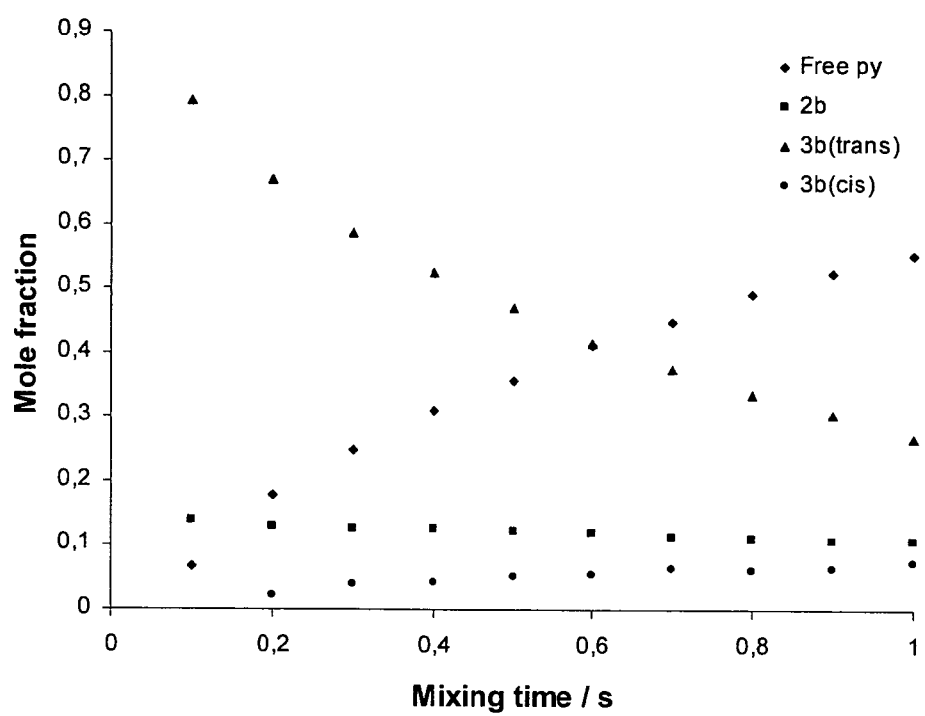
FIG. 3 is a plot of the fraction of overall signal integration for pyridine ligands of $[Ir(P\{p\text{-tolyl}\}_3)(H)_2(py)_3]^+$, $[Ir(P\{p\text{-tolyl}\}_3)_2(H)_2(py)_2]^+$ and polarised free pyridine.

FIG. 2 illustrates spectral traces which confirm that the $^{15}$N signal of free pyridine and other suitable ligands were enhanced using this approach. Further, FIG. 2 illustrates RF based magnetization transfer of polarization into the hyperpolarizable substrate. FIG. 3 demonstrates that the degree of polarization transfer depends on the contact time (mixing time) and transfer time.

EXAMPLE 4

Figure 4:
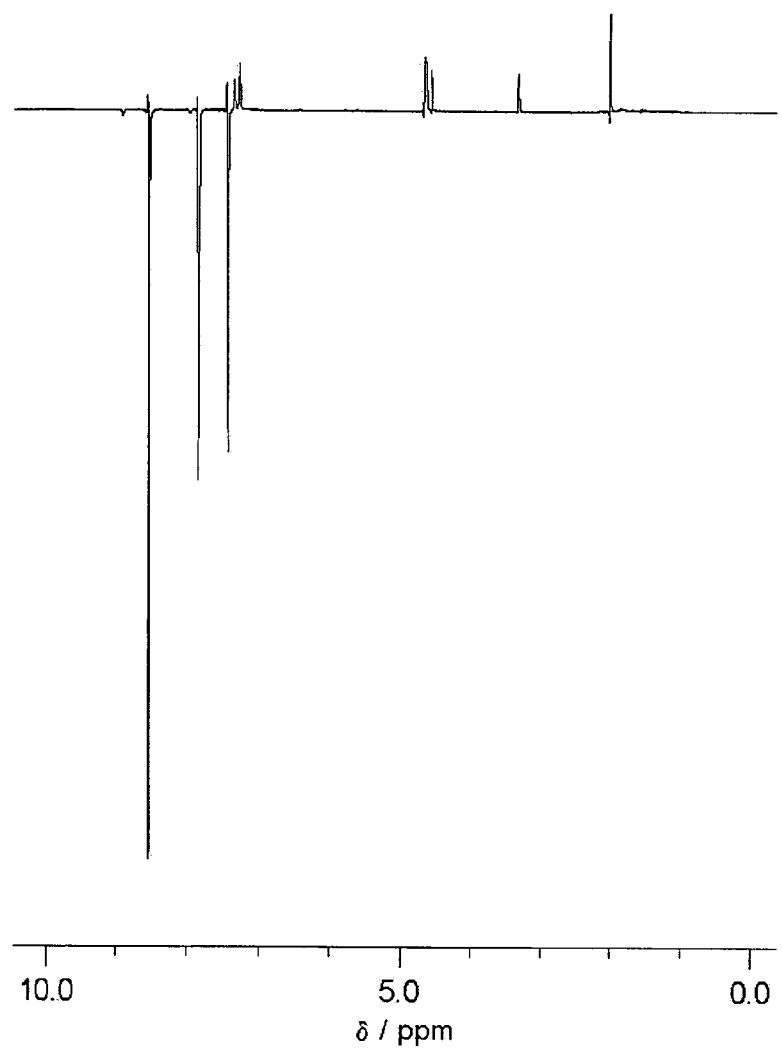
FIG. 4 is a $^1H$ NMR spectrum of a sample using the $PCy_3$ supported iridium complex showing emission signals for spontaneously polarised pyridine.

Spontaneous Polarisation Transfer 1 mg of a hydrogenatable complex such as [Ir(COD)(PR$_3$)$_2$]BF$_4$, [Ir(COD)(PR$_3$)(py)]BF$_4$, or [Ir(COD)(py)$_2$]BF$_4$/PR$_3$ where R is a suitable donor such as Cy, was dissolved in 500 µL of d$_4$-methanol in an NMR tube fitted with a Young's tap top. To this sample was added approximately 1 mg of substrate to be polarised (and 1 to 10 µL of a suitable hydrogen acceptor such as 1-phenylprop-1-yne if necessary). The samples were then degassed and then pressurised to 3 to 3.5 bar with p-H$_2$. The samples were then shaken to dissolve the gas and immediately transferred into the spectrometer. Recording of $^1$H NMR (or a single scan heteronuclear spectrum, e.g. $^{13}$C, $^{15}$N) spectra commenced as soon as the sample arrived in the probe head. Under these conditions specific substrate resonances were polarised, as illustrated in FIG. 4. Procedure for Testing Effectiveness of Phosphine Ligands 2 mg of [Ir(COD)(py)$_2$]BF$_4$ (COD=1,5-cyclooctadiene, py=pyridine) was dissolved in 500 µL degassed d$_4$-methanol containing 1 µL of pyridine in an NMR tube fitted with a Young's tap top in a glove box. To this sample was added 1 to 2 equivalents of the desired phosphine to generate [Ir(COD)(PR$_3$))$_x$(py)$_y$]$^+$ in situ. After locking and shimming the spectrometer on the sample, the sample was then pressurised to 3 to 3.5 bar with p-H$_2$, shaken to dissolve the gas and immediately transferred into the spectrometer. Recording of spectra commenced as soon as the sample arrived in the probe head. Effectiveness of the polarisation was estimated from comparative integration of polarised and solvent signals in the $^1$H NMR spectrum.

Based on this procedure, the phosphines PCy$_3$ and tris-(ortho-tolyl)-phosphine were found to provide particularly enhanced signals.

EXAMPLE 5

Field Dependence of Spontaneous Polarization Transfer

In Example 5 it is shown that treatment (here shaking) of the entirety of prepared fluid (here containing p-H$_2$), provided compound (here pyridine) and provided template (here an Ir metal complex) by shaking in different magnetic fields results in a variation of the polarization transfer. This offers a possibility to control and optimize the polarization transfer. Note that also the field orientation influences the signal (namely the signal phase).

Figure 5A:
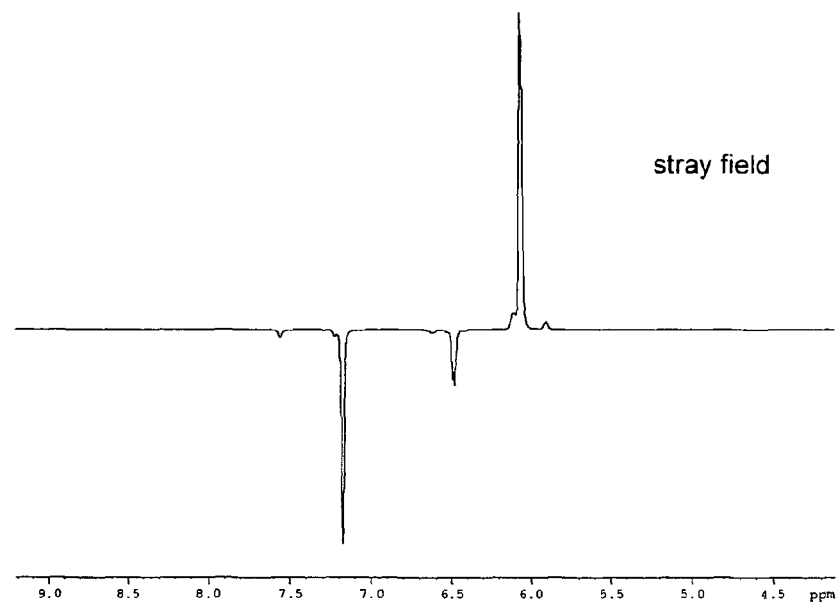
FIG. 5a $^1H$ NMR spectrum of free pyridine when sample is shaken outside the stray field of the spectromer.
Figure 5B:
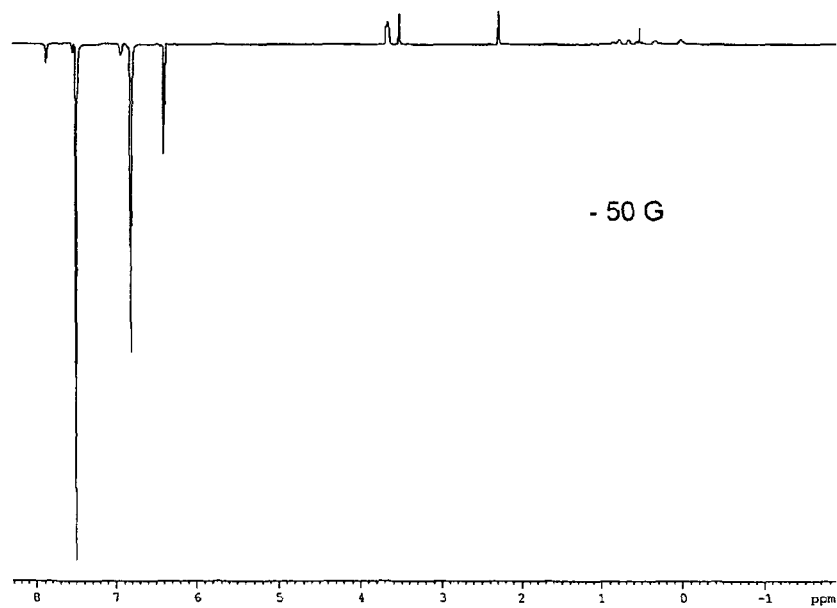
FIG. 5b $^1H$ NMR spectrum of free pyridine when sample is shaken outside around the spectrometer with a field of approximately −50 G (−5*10$^{-3}$ T)
Figure 5C:
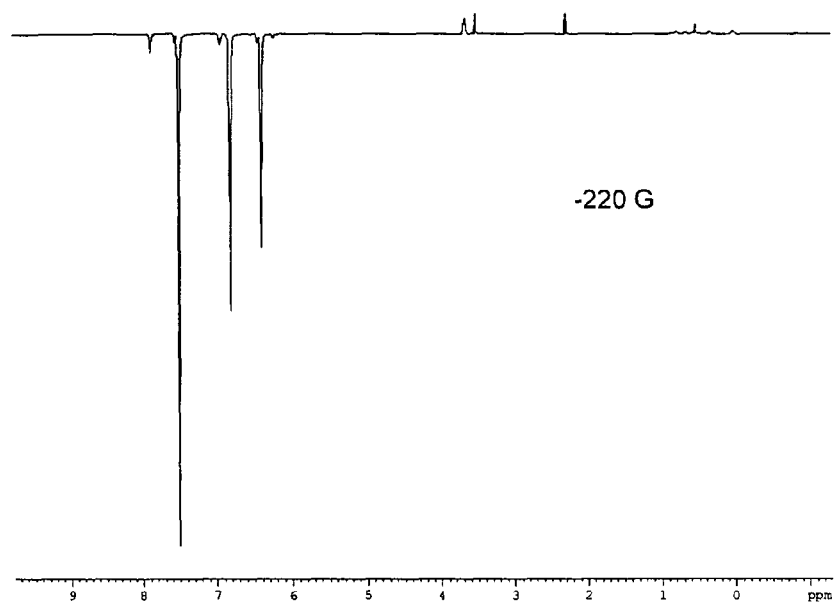
FIG. 5c $^1H$ NMR spectrum of free pyridine when sample is in a region around the spectrometer with a field of approximately −220 G (−2.2*10$^{-2}$ T)
Figure 5D:
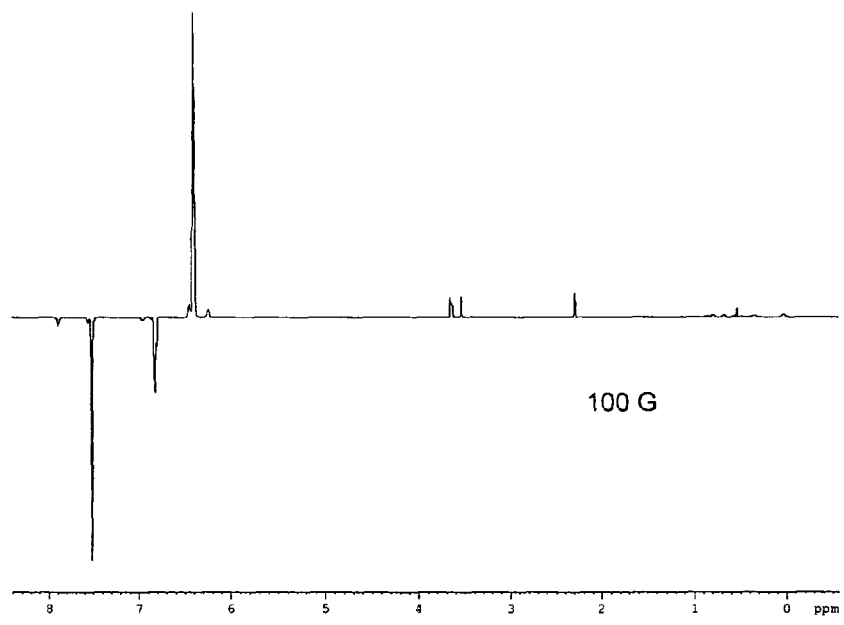
FIG. 5d $^1H$ NMR spectrum of free pyridine when sample is in a region around the spectrometer with a field of approximately 100 G (10$^{-2}$ T)

1 to 3 mg of [Ir(COD)(PR$_3$)(py)]BF$_4$, (where PR$_3$=PCy$_3$ or PPhCy$_2$) was dissolved in 600 μL of d$_4$-methanol in an NMR tube fitted with a Young's tap top. To this sample was added approximately 5 mg of substrate to be polarised. The sample was then degassed and then pressurised to 3 to 3.5 bar with p-H$_2$. The samples were then shaken outside the stray field of the spectrometer (i.e. in earth magnetic field) to dissolve the gas and immediately transferred into the spectrometer. Recording of $^1$H NMR spectra, unlocked, commenced as soon as the sample arrived in the probe head. Under these conditions specific substrate resonances were polarised, as illustrated in FIG. 5a. When the sample was removed from the spectrometer and shaken in regions of differing magnetic field about the spectrometer, the pattern of the polarised resonances was changed, as shown in FIG. 5b at −50 G, in FIG. 5c at −220 G, and FIG. 5d at 100 G. The positive or negative signs of the magnetic fields refer to locations with essentially reversed local magnetic field directions.

EXAMPLE 6

Polarization Transfer to Different Substrates (Compounds) with Different Donors

In Example 6 it is illustrated that spontaneous polarization transfer can be achieved to a variety of substrates (other than pyridine) including N-donor ligands, NH-donor ligands, and S-donor ligands.

Figure 6A:
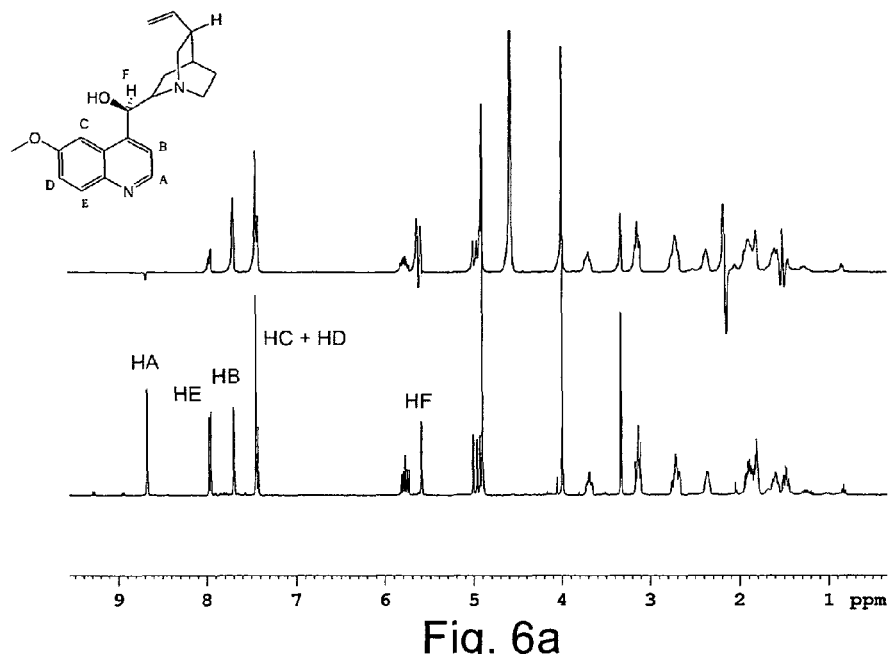
FIG. 6a: $^1H$ NMR spectrum of free Quinine (upper spectrum) and spectrum of the same NMR $d_4$-methanol sample containing $[Ir(COD)(PCy_3)(MeCN)]BF_4$ and Quinine (below)
Figure 6B:
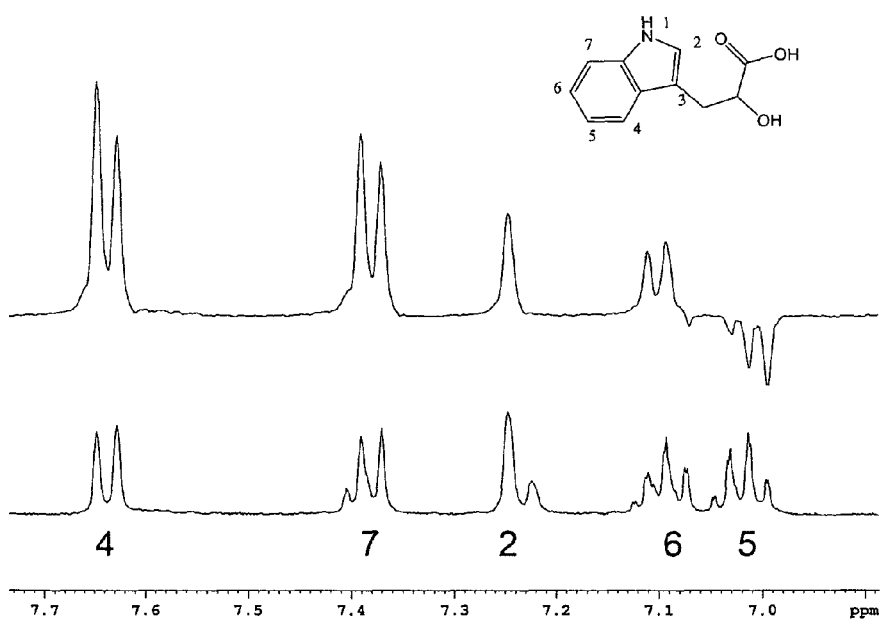
FIG. 6b: $^1H$ NMR spectrum of free Indole-3-lactic acid (upper spectrum) and spectrum of the same NMR $d_4$-methanol sample containing $[Ir(COD)(PCy_3)(MeCN)]BF_4$ and Indole-3-lactic acid (below)
Figure 6C:
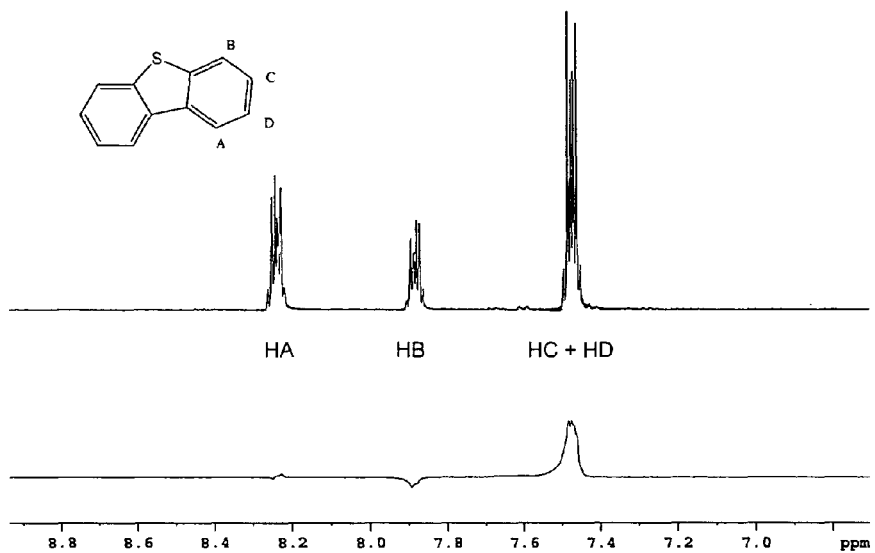
FIG. 6c $^1H$ NMR spectrum of free dibenzothiophene (lower spectrum) and spectrum of the same NMR $d_4$-methanol sample containing $[Ir(COD)(PCy_3)(MeCN)]BF_4$ and dibenzothiophene (above)

1 to 3 mg of [Ir(COD)(PCy$_3$)(MeCN)]BF$_4$ was dissolved in 600 μL of d$_4$-methanol in an NMR tube fitted with a Young's tap top. To this sample was added approximately 5 mg of substrate to be polarised. The sample was then degassed and then pressurised to 3 to 3.5 bar with p-H$_2$. The samples were then shaken outside the stray field of the spectrometer to dissolve the gas and immediately transferred into the spectrometer. Recording of $^1$H NMR spectra, unlocked, commenced as soon as the sample arrived in the probe head. Under these conditions specific substrate resonances were polarised, as illustrated in FIG. 6a for Quinine (N), in FIG. 6b for indole-3-lactic acid (NH), and FIG. 6c for dibenzothiophene (S).

EXAMPLE 7

Polarization Transfer to $^{13}$C, $^{31}$P and $^{19}$F

The Example shows that polarization can be transferred not only to $^{15}$N, but equally well to other hyperpolarizable nuclei.

Figure 7A:
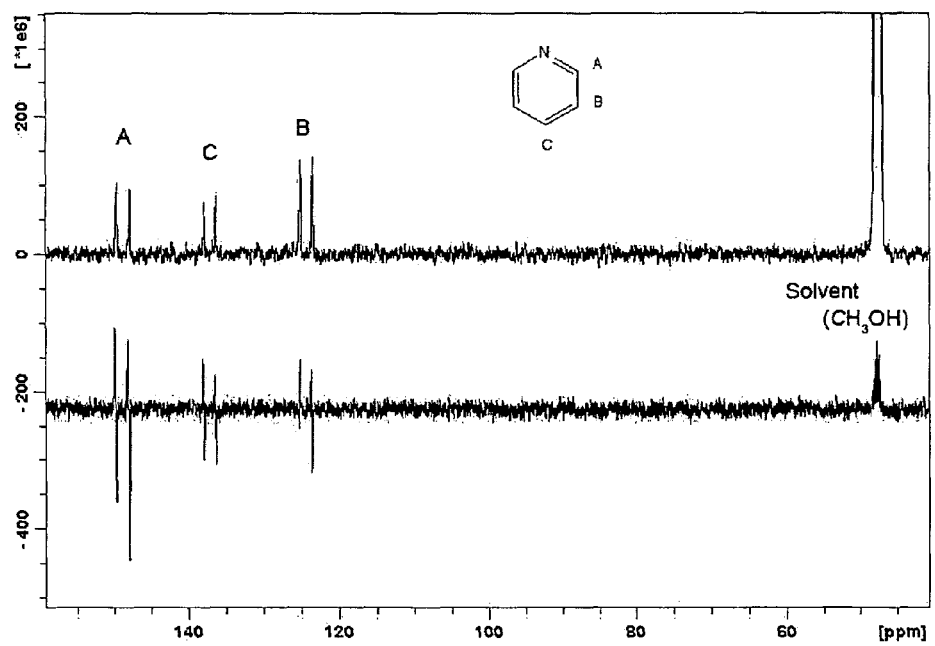
FIG. 7a: Single scan fully coupled $^{13}C$ NMR spectrum (313 K, $d_4$-methanol; below) showing hyperpolarised resonances for free pyridine (natural abundance $^{13}C$) and fully coupled $^{13}C$ spectrum of the same sample after 1536 scans acquired after hyperpolarisation had relaxed (above)
Figure 7B:
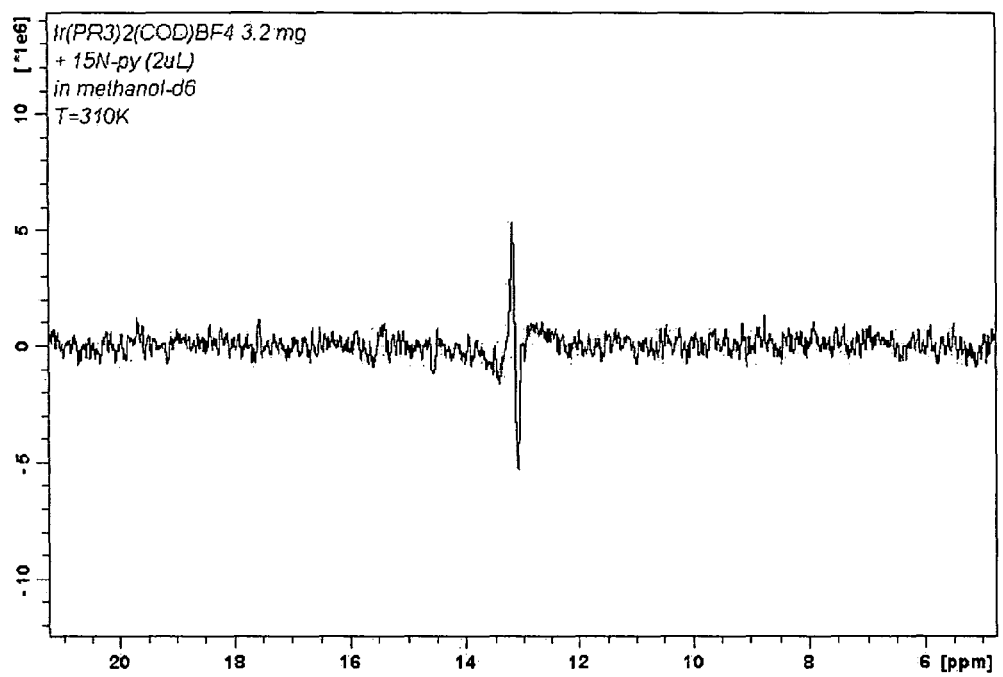
FIG. 7b: $^{31}P$ NMR spectrum showing polarisation of bound tricyclohexyphosphine of a NMR $d_4$-methanol sample containing $[Ir(COD)(PCy_3)(py)]BF_4$, pyridine and para-hydrogen.

In all cases, 1 to 3 mg of [Ir(COD)(PR$_3$)(py)]BF$_4$, (where PR$_3$=PCy$_3$. PPhCy$_2$) was dissolved in 600 μL of d$_4$-methanol in an NMR tube fitted with a Young's tap top. To this sample was added approximately 5 mg of substrate to be polarised (see below). The sample was then degassed and then pressurised to 3 to 3.5 bar with p-H$_2$. The samples were then shaken outside the stray field of the spectrometer to dissolve the gas and immediately transferred into the spectrometer. Recording of the spectra, unlocked, commenced as soon as the sample arrived in the probe head.
Polarization of $^{13}$C Resonances of Pyridine A sample containing [Ir(COD)(PCy$_3$)(py)]BF$_4$ and ca. 5 μL of natural abundance—$^{13}$C pyridine as the substrate was prepared as described above. This sample was heated to 313 K in a thermostated NMR spectrometer, ejected from the spectrometer, shaken outside of the stray field of the NMR magnet and reintroduced into the spectrometer as described above. A single scan $^{13}$C NMR experiment (with a 90° pulse) was then performed on the sample without proton decoupling. When this experiment was processed three sets of antiphase resonances were clearly shown, corresponding to free pyridine (see FIG. 7a). When the same experiment was repeated a few minutes after the sample had been shaken and reintroduced into the NMR spectrometer, the resonances for free pyridine were not visible. The enhancement level was estimated by acquiring a fully coupled $^{13}$C NMR experiment with 1536 scans and comparing the signal to noise (S/N) ratio of this spectrum and the single scan experiment, both processed in magnitude calculation: the S/N ratio for the single scan experiment with hyperpolarised free pyridine calculated in this way is 15.2, while for the non-polarised sample after 1536 scan is 6.78.
Polarization of $^{31}$P of Tricyclohexylphosphine A sample containing [Ir(COD)(PCy$_3$)(py)]BF$_4$ and ca. 5 μL of $^{15}$N labelled pyridine as the substrate was prepared as described above. This sample was heated to 310 K in a thermostated NMR spectrometer, ejected from the spectrometer, shaken outside of the stray field of the NMR magnet and reintroduced into the spectrometer as described below. A single scan $^{31}$P NMR experiment (with a 90° pulse) was then performed on the sample without proton decoupling. When this experiment was processed a single antiphase resonance for the iridium-coordinated tricyclohexylphosphine was clearly shown (see FIG. 7b). When the same experiment was repeated a few minutes after the sample had been shaken and reintroduced into the NMR spectrometer, the resonance was not visible.
Polarisation of $^{19}$F Resonance of 3-fluoropyridine A sample containing [Ir(COD)(PCy$_3$)(py)]BF$_4$ and 5 μL of 3-fluoropyridine as the substrate was prepared as described above. This sample was heated to 300 K in a thermostated NMR spectrometer, ejected from the spectrometer, shaken outside of the stray field of the NMR magnet and reintroduced into the spectrometer as described above. A single scan $^{19}$F NMR experiment (with a 90° pulse) was then performed on the sample.

Figure 7C:
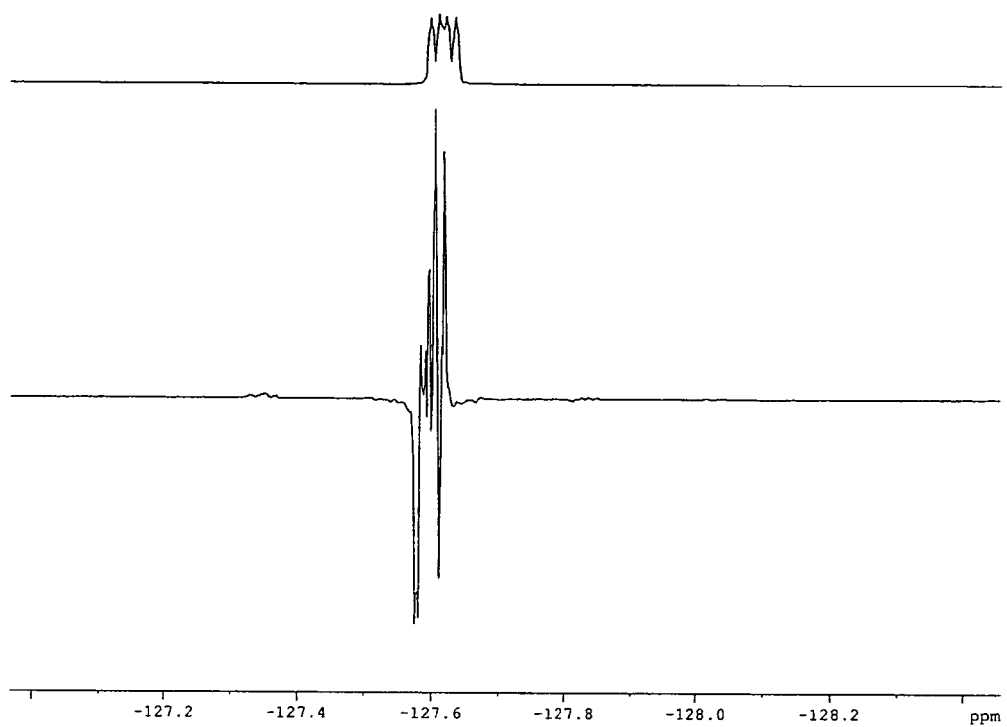
FIG. 7c: Single scan $^{19}F$ NMR spectra (300 K, $d_4$-methanol) showing hyperpolarised resonances for free 3-fluoropyridine (bottom) and a spectrum of the same sample d after hyperpolarisation had relaxed (top)

When this experiment was processed an antiphase resonance was clearly shown, corresponding to free 3-fluoropyridine (see FIG. 7c). When the same experiment was repeated a few minutes after the sample had been shaken and reintroduced into the NMR spectrometer, the resonance for free pyridine was much reduced in intensity. The enhancement level was estimated by comparing the signal to noise (S/N) ratio of the two experiments, both processed in magnitude calculation: the S/N ratio for the single scan experiment with hyperpolarised free 3-fluoropyridine calculated in this way is 1146, while for the non-polarised sample is 282.

EXAMPLE 8

Polarization of $^{13}$C Resonances of CO$_2$

This Example shows that polarization can be transferred even to gases such as CO$_2$, in accordance with the invention.

Figure 8:
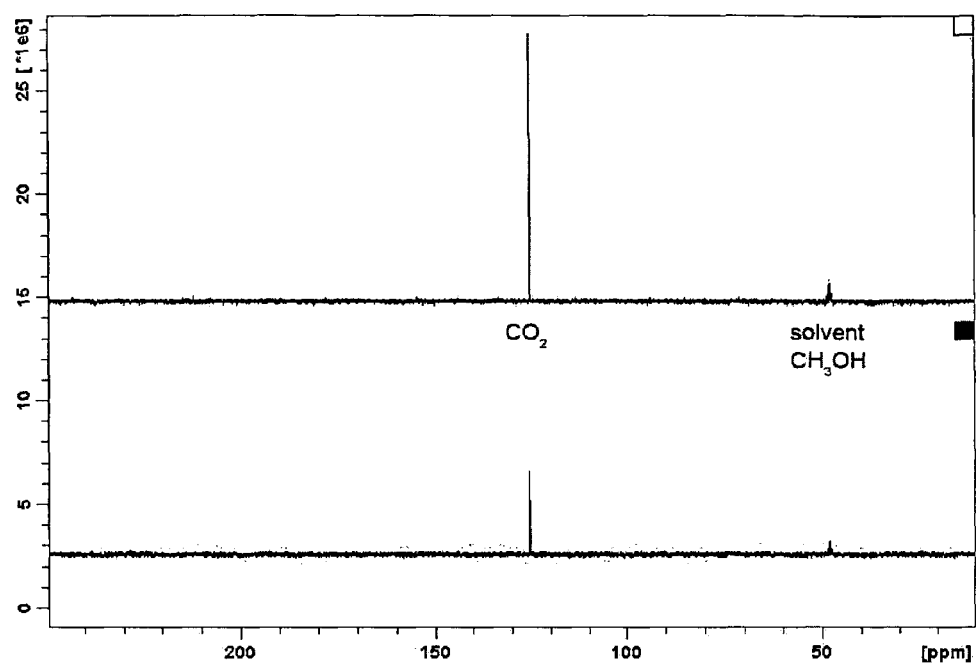
FIG. 8: Single scan fully coupled $^{13}C$ NMR spectrum (298 K, $d_4$-methanol; below) showing the resonance for free $^{13}CO_2$ obtained immediately after shaking the sample outside the stray field of the NMR spectrometer and $^{13}C$ spectrum of the same sample after several minutes (top).

A sample containing [Ir(COD)(PCy$_3$)(py)]BF$_4$ was prepared as described above. In this case a mixture of the polarisable substrate $^{13}$CO$_2$ and paraHydrogen was introduced over the degassed solution of metal complex (combined pressure: ca. 3 bar). This sample was shaken outside of the stray field of the NMR magnet and reintroduced into the spectrometer as described above. A single scan $^{13}$C NMR experiment was then performed on the sample without proton decoupling immediately after reintroducing the sample. After a suitable amount of time, another $^{13}$C NMR experiment was recorded to be used as a control. When the first experiment, obtained immediately after shaking and reintroducing the sample into the spectrometer, and the latest experiments were compared, it was evident that the resonance for free $CO_2$ was less intense in the first experiment (see FIG. 8). Comparison of the signal to noise ratios for the $CO_2$ resonances revealed that it was 3.2 times higher in the spectrum acquired after the polarization.

EXAMPLE 9

Polarization of Hydrogen Using Zeolites

The Example shows that using zeolites as template, polarization could be transferred using para-hadrogen as the symmetric molecule.

Zeolite was placed in a schlenk tube and heated under vacuum at 110° C. for 24 hours. The tube was then transferred to the glove box and the zeolite stored under $N_2$.

An NMR tube equipped with a Young's tap was charged with approximately 5-6 beads of zeolite, 5 μL pyridine and 600 μL MeOD (=$d_4$-methanol). The sample was degassed on the high vacuum line.

Para-hydrogen was placed over the sample, it was then shaken vigorously and immediately put in the NMR spectrometer. Spectra were run to observe any transfer in magnetization.

The sample was removed, shaken vigorously and returned to the spectrometer. The sample was degassed, fresh para-hydrogen placed over and the experiments repeated.

A second experiment was carried out using diethyl ether as the substrate instead of pyridine.

The experimental results indicate that the ortho-hydrogen content has increased, from which can be concluded that para-hydrogen has transferred its polarization away via the zeolite and transformed into ortho-hydrogen.

Introduction to the Invention with Special Respect to a Variant of the Invention Using Para-Hydrogen as the Source of Nuclear Spin Polarization In the following, an overview over the present invention is given with respect to a use of para-hydrogen as the symmetric molecule. However, para-hydrogen should be understood here as an example, and the information given below can also transferred to other types of symmetric molecules. In the same way, a metal complex should be understood as an example for a site of ordered environment, and other types of templates offering sites of ordered environment may be applied alternatively.

According to the invention, by suitably arranging parahydrogen or a derivative thereof and a hyperpolarizable nucleus in an ordered environment, hyperpolarization can be transferred directly from the parahydrogen nuclei to the hyperpolarizable nucleus, i.e. without the need to chemically incorporate the parahydrogen into a compound comprising the hyperpolarizable nucleus. The hyperpolarized state of the nucleus is substantially retained when the compound is removed from the ordered environment.

Accordingly, the present invention provides a process for producing a compound comprising hyperpolarized nucleus, which comprises:
  (a) arranging parahydrogen or a hyperpolarized derivative thereof and a compound comprising a hyperpolarizable nucleus in an ordered environment such that hyperpolarization is directly transferable from the parahydrogen or derivative to the hyperpolarizable nucleus;
  (b) directly transferring hyperpolarization from the parahydrogen or derivative to the hyperpolarizable nucleus; and
  (c) separating the compound comprising the hyperpolarized nucleus from the ordered environment.

By way of illustration, a process of the invention may involve the use of a metal complex comprising a pair of hydride ligands whose nuclei are hyperpolarized and a ligand comprising a hyperpolarizable nucleus. When the ligands are suitably arranged about the metal centre, hyperpolarization can be transferred directly from the hydride ligands to the hyperpolarizable nucleus.

Thus, the invention includes, but is not limited to, a process for producing a compound comprising a hyperpolarized nucleus from a hydrogenated metal complex, wherein the complex comprises a pair of hydride ligands whose nuclei are hyperpolarized and a ligand comprising a hyperpolarizable nucleus, and wherein the hydride ligands are arranged such that hyperpolarization is directly transferable from the hydride ligands to the hyperpolarizable nucleus, the process comprising directly transferring hyperpolarization from the hydride ligands to the hyperpolarizable nucleus and separating the ligand comprising the hyperpolarized nucleus from the complex.

The invention also provides a device for producing a compound comprising a hyperpolarized nucleus, which comprises a reaction chamber comprising:
  a) an inlet for a fluid enriched with para-hydrogen; and
  b) a metal complex attached to a support, wherein the complex is hydrogenatable or hydrogenated with parahydrogen.

The metal complex of said device may comprise a ligand which is a compound comprising a hyperpolarizable nucleus. The device may further comprise an inlet for a solution comprising said ligand in unbound form.

Also provided is a hydrogenated metal complex comprising a pair of hydride ligands whose nuclei are hyperpolarized and a ligand comprising a hyperpolarizable nucleus, wherein the hydride ligands are arranged such hyperpolarization is directly transferable to the hyperpolarizable nucleus.

Compounds obtained by a process of the invention may be useful as magnetic resonance (MR) imaging agents. Accordingly, the use of compounds polarized in this way in diagnosis or therapy also forms part of the invention. In one aspect, the invention provides a composition comprising a compound comprising a nucleus which has been hyperpolarized by a process of the invention and a physiologically acceptable carrier or excipient.

Processes of the present invention are advantageous in several respects over conventional hyperpolarization processes. A process of the invention may be used to hyperpolarize nuclei in a wide variety of compounds, without requiring that the compounds be capable of undergoing hydrogenation. For example, many metabolites comprise heteroatoms such as nitrogen, phosphorus or carbon, all of which are capable of coordinating to transition metal centres via suitable interactions. Thus, the invention is particularly suited for forming metabolic magnetic resonance (MR) contrast agents. The ligand can become substantially polarized by cycling of this process. Furthermore, addition of dihydrogen to transition metal complexes is a reversible process or can be promoted by the addition of a suitable sacrificial hydrogen acceptor or light source. Thus, with the right transition metal system, a continuous supply of parahydrogen can be provided that is in rapid equilibrium with the dihydride metal complex, thereby promoting the generation of a hyperpolarized metal complex.

Details on Inventive Embodiments With Special Respect to the Variant of the Invention Using Para-Hydrogen as the Source of Nuclear Spin Polarization In the following, details on inventive embodiments of the present invention are described with respect to a use of parahydrogen as the symmetric molecule. However, para-hydrogen should be understood here as an example, and the details listed below can also be applied with other types of symmetric molecules. In the same way, a metal complex should be understood as an example for a site of ordered environment, and other types of templates offering sites of ordered environment may be applied alternatively.

According to the present invention, parahydrogen or a hyperpolarized derivative thereof and a compound comprising a hyperpolarizable nucleus are arranged in an ordered environment such that hyperpolarization is directly transferable from the parahydrogen or derivative to the hyperpolarizable nucleus. The hyperpolarizable nucleus is then hyperpolarized by directly transferring hyperpolarization from the parahydrogen or derivative to the hyperpolarizable nucleus. The compound comprising the hyperpolarized nucleus can then be removed from the ordered environment and used as required, e.g. as a contrast agent.

A process of the invention utilises parahydrogen or a hyperpolarized derivative thereof. The hyperpolarized derivative may comprise a pair of hydride ligands whose nuclei are hyperpolarized. Hyperpolarization is transferred directly from the parahydrogen or derivative to a compound comprising one or more hyperpolarizable nuclei. By way of example, the or each hyperpolarizable nucleus may be selected from $^1H$, $^{13}C$, $^{15}N$, $^{29}Si$ and $^{31}P$ nuclei. An ordered environment is utilised to ensure that the parahydrogen or derivative and the hyperpolarizable nucleus are suitably arranged so as to facilitate direct transfer of hyperpolarization. Suitable ordered environments will be apparent to those skilled in the art and include complexes, in particular metal complexes, and the like.

The compound comprising the hyperpolarizable nucleus may be organic or inorganic in nature. Typically, the compound will comprise one or more atoms selected from hydrogen, carbon, nitrogen, oxygen, silicon, sulphur, fluorine and phosphorus. Where the compound is a ligand, it may be a mono-, or multi-dentate ligand. Included are compounds, especially ligands, comprising one or more heterocyclic groups, in particular one or more heterocyclic groups comprising $^{15}N$. For example, the compound may comprise one or more groups selected from pyridine and derivatives thereof (e.g. 3- or 4-methylpyridine), nicotinamide, nicotine, pyridazine, purine, quinoline, quinazoline, quinoxaline and quinine. In one embodiment, the compound does not comprise an aliphatic unsaturated carbon-carbon bond. Of mention are compounds which are metabolites. Thus, the compound comprising the hyperpolarizable nucleus may be selected from amino acids, proteins, carbohydrates, nucleotides, drugs, prodrugs, coenzymes, cofactors and other materials that contain hyperpolarizable nuclei. Where the compound is a ligand, it is preferably labile, such that it can readily dissociate from the metal complex, e.g. when in equilibrium with unbound ligand in solution.

In a preferred embodiment, the present invention involves the use of a metal complex which has been hydrogenated with para-hydrogen and which comprises a ligand which is a compound comprising a hyperpolarizable nucleus. The ligand may comprise one or more hyperpolarizable nuclei. By way of example, the or each hyperpolarizable nucleus may be selected from $^1H$, $^{13}C$, $^{15}N$, $^{19}F$, $^{29}Si$ and $^{31}P$ nuclei. Of mention are ligands comprising one or more $^{13}C$ or $^{15}N$ nuclei, in particular one or more $^{15}N$ nuclei. In one embodiment, the ligand is attached directly to the metal via an atom comprising the said hyperpolarizable nucleus.

The metal complex will usually be a transition metal complex, for example comprising a metal atom selected from Ru, Rh, Ir, W, Pd and Pt. The complex will usually comprise one or more ligands in addition to the ligand comprising the hyperpolarizable nucleus. These one or more other ligands may comprise organic or inorganic ligands and may be mono-, bi- or multidentate in nature. These one or more remaining ligands may play a role in controlling the activity and stability of the metal centre. In one embodiment, the metal complex comprises one or more phosphine ligands in addition to the ligand to be hyperpolarized. The metal complex may be attached to a solid support, for example a polymer support. Attachment will usually be made through a ligand which links the metal centre to the support. Suitable linkers are known in the art. For example, the linker may comprise one or more in-chain atoms selected from C, O, N, S, P and Si. The linker comprises a siloxane moiety for attachment to the support and/or a phosphine moiety for attachment to the metal of the complex. In embodiments, the linker is a group of the following formula: —O—Si(OMe)$_2$—(CH$_2$)$_n$—P(Cy)$_2$—, wherein n is 0 upwards (e.g. 0, 1, 2, 3, 4, 5 or 6) and Cy is cyclohexyl.

In one embodiment, the hydrogenated metal complex is an octahedral complex. In this case, the complex may comprise hydride ligands arranged relatively cis and one or more ligands comprising a hyperpolarizable nucleus arranged trans thereto. One of the remaining ligands may, for example, act as a linker which tethers the complex to a support.

The hydrogenated metal complex may be obtained by reacting parahydrogen with a hydrogenatable metal complex comprising the ligand comprising the hyperpolarizable nucleus. Alternatively, the hydrogenated metal complex may be obtained by reacting a ligand comprising the hyperpolarizable nucleus with a metal complex hydrogenated with parahydrogen.

Hydrogenation of the complex may be achieved by contacting the complex with a fluid, typically a solution, containing dissolved para-hydrogen, preferably such that the resulting hydride ligands are in equilibrium with the para-hydrogen in solution. Fluids enriched with para-hydrogen are particularly suitable in this regard. The term "enriched hydrogen" as used herein includes reference to hydrogen in which there is a higher than equilibrium proportion of para-hydrogen, for example where the proportion of para-hydrogen is more than 25%, e.g. more than 30%, e.g. 45% or more, e.g. 60% or more, e.g. 90% or more, in particular 99% or more. Enriched hydrogen may be obtained catalytically at low temperatures e.g. at 160 K or less, preferably at 80 K or less or more preferably at about 20 K. The parahydrogen thus formed may be stored for long periods, preferably at low temperature, e.g. 18 to 20 K. Alternatively the parahydrogen may be stored in pressurized gas form in containers with non-magnetic and non-paramagnetic inner surfaces, e.g. a gold or deuterated polymer coated container. Parahydrogen may also be obtained by electrolysis. The hydrogenation step may be performed in the liquid or gaseous phase, and preferably in the absence of materials which would promote relaxation.

The ligands are arranged such that the hyperpolarization is directly transferable from the hydride ligands to hyperpolarizable nucleus, i.e. hyperpolarization is transferable without first chemically incorporating the hydride ligands into the compound comprising the hyperpolarizable nucleus. When a metal complex is hydrogenated with para-hydrogen, the resulting hydride ligands are normally formed in a cis arrangement. In this arrangement, transfer of hyperpolarization from the hydride ligands to the hyperpolarizable nucleus will normally be possible, especially when the ligand comprising the hyperpolarizable nucleus is located trans to the hydride ligands.

Hyperpolarization of the hyperpolarizable nucleus by the parahydrogen or derivative ligands may occur spontaneously. In general, spontaneous polarization will occur when the transitions associated with the NMR signals are close in energy and therefore mix. This situation can be readily achieved in a low field, but may also be achieved by the application of a suitable train of radio frequencies.

Spontaneous transfer can in some cases be enhanced further by pulse sequences of electromagnetic radiation that can be applied to the system which will result in polarization transfer. Examples of suitable sequences can be found in the Figures herein and in Blazina et al, Dalton Trans., 2004, 2601-2609.

After hyperpolarization has been transferred, the compound comprising the hyperpolarized nucleus can then be separated from the ordered environment and the parahydrogen or derivative thereof. Separation may be achieved using physical and or chemical means. Where a hydrogenated metal complex forms the ordered environment, the ligand comprising the hyperpolarized nucleus is separated from the complex. In this regard, the ligand is preferably chemically or physically labile. Where the ligand is labile, dissociation of the ligand from the complex may be achieved by contacting the complex with a solution comprising the ligand in unbound form. Equilibrium may be established to between the bound and unbound ligand, facilitating dissociation of the hyperpolarized ligand from the nucleus.

Hyperpolarized compounds of the invention may be suitable for use in high resolution NMR experiments. In this case, the compound should preferably be strongly polarizable (for example, to a level of greater than 5%, preferably greater than 10%, more preferably greater than 25%). Collection of $^1H$, $^{13}C$, $^{15}N$, $^{31}P$ or $^{29}Si$ signals should be facilitated.

The invention is particularly suited to the production of MR imaging agents. In this case, the compound should preferably be strongly polarizable (for example, to a level of greater than 5%, preferably greater than 10%, more preferably greater than 25%) and have a non-hydrogen MR imaging nucleus with a long $T_1$ relaxation time under physiological conditions, e.g. $^{13}C$, $^{15}N$ or $^{29}Si$. By a long $T_1$ relaxation time is meant that $T_1$ is such that once polarised, the MR imaging agent will remain so for a period sufficiently long to allow the imaging procedure to be carried out in a comfortable time span. Significant polarization should therefore be retained for at least 1 s, preferably for at least 60 s, more preferably for at least 100 s and especially for 1000 s or longer. Furthermore, the chemical shift, or even better the coupling constant of the signal from the imaging nucleus should preferably be influenced by physiological parameters (e.g. morphology, pH, metabolism, temperature, oxygen tension or calcium concentration). For example, influence by pH can be used as a general disease marker, whilst influence by metabolism may be a cancer marker. Alternatively, the MR imaging agent may conveniently be a material which is transformed (e.g. at a rate such that its half-life is no more than $10 \times T_1$ of the reporter nucleus, preferably no more than $1 \times T_1$) in the subject under study to a material in which the reporter nucleus has a different coupling constant or chemical shift.

The MR imaging agents may be administered to a sample and the sample subsequently exposed to radiation of a frequency selected to excite nuclear spin transitions of one or more hyperpolarized nuclei present in the imaging agent. The magnetic resonance signals of the nuclei can then be detected. The detected signals can then be used to generate an image, biological functional data or dynamic flow data.

MR imaging agents may be used to image a subject, for example, selected from a human or animal, a cell culture, a membrane-free culture or a chemical reaction medium. Thus, it may be preferable for the MR imaging agents to have negligible toxicity. Such agents have both in vitro and in vivo usage.

The MR imaging agent may be administered parenterally, e.g. by bolus injection, by intravenous or intra-arterial injection or, where the lungs are to be imaged, in spray form, e.g. by aerosol spray. Oral and rectal administration may also be used.

MR imaging agents may be conveniently formulated with conventional pharmaceutical or veterinary carriers or excipients. Formulations of the invention may thus comprise one or more components selected from stabilizers, antioxidants, osmolality adjusting agents, solubilizing agents, emulsifiers, viscosity enhancers and buffers. Preferably, these components are not paramagnetic, superparamagnetic, ferromagnetic or ferrimagnetic. The formulation may be in forms suitable for parenteral (e.g. intravenous or intraarterial) or enteral (e.g. oral or rectal) application, for example for application directly into body cavities having external voidance ducts (such as the lungs, the gastrointestinal tract, the bladder and the uterus), or for injection or infusion into the cardiovascular system. However, solutions, suspensions and dispersions in physiological tolerable carriers (e.g. water) will generally be preferred.

Where the MR imaging agent is to be injected, it may be convenient to inject simultaneously at a series of administration sites such that a greater proportion of the vascular tree may be visualized before the polarisation is lost through relaxation. Intra-arterial injection is useful for preparing angiograms and intravenous injection for imaging larger arteries and the vascular tree.

Parenterally administrable forms should of course be sterile and free from physiologically unacceptable agents and from paramagnetic, superparamagnetic, ferromagnetic or ferrimagnetic contaminants, and should have low osmolality to minimize irritation or other adverse effects upon administration and thus the formulation should preferably be isotonic or slightly hypertonic. Suitable vehicles include aqueous vehicles customarily used for administering parenteral solutions such as sodium chloride solution, Ringer's solution, dextrose solution, dextrose and sodium Chloride solution, lactated Ringer's solution and other solutions such as are described in Remington's Pharmaceutical Sciences, 15th ed., Easton: Mack Publishing Co., pp. 1405-1412 and 1461-1487 (1975) and The National Formulary XIV, 14th ed. Washington: American Pharmaceutical Association (1975). The compositions can contain preservatives, antimicrobial agents, buffers and antioxidants conventionally used for parenteral solutions, excipients and other additives which are compatible with the MR imaging agents and which will not interfere with the manufacture, storage or use of the products.

For use in in vivo imaging, the formulation, which normally will be substantially isotonic, may conveniently be administered at a concentration sufficient to yield a 1 µM to 1M concentration of the MR imaging agent in the imaging zone. However, the precise concentration and dosage will of course depend upon a range of factors such as toxicity, the organ targeting ability of the MR imaging agent, and the administration route. The optimum concentration for the MR imaging agent represents a balance between various factors. In general, optimum concentrations will typically range from about 0:1 mM to about 10 M, especially from about 0.2 mM to about 1M, more especially from about 0.5 mM to about 500 mM. Formulations for intravenous or intraarterial administration may, for example, contain the MR imaging agent in concentrations of from about 10 mM to about 10 M, especially from about 50 mM to about 500 mM. For bolus injection the concentration may conveniently range from about 0.1 mM to about 10M, especially from about 0.2 mM to about 10 M, in particular from about 0.5 mM to 1M, more particularly from about 10 mM to about 500 mM, yet still more particularly from about 10 mM to about 300 mM.

The dosages of the MR imaging agent used according to the process of the present invention will vary according to the precise nature of the MR imaging agents used, of the tissue or organ of interest and of the measuring apparatus. Typically, the dosage should be kept as low as possible whilst still achieving a detectable contrast effect. By way of example, the dosage may range from 1 to 1000 mg/kg, e.g. from 2 to 500 mg/kg, especially from 3 to 300 mg/kg.

Once the MR imaging agent has been administered to the subject, the MR signals may be detected using procedures known in the art. For example, it may be advantageous to use fast single shot imaging sequences e.g. EPI, RARE or FSE. MR signals may be conveniently converted into two- or three-dimensional image data or into functional, flow or perfusion data by conventional manipulations. By imaging, it will be appreciated that not just production of two- or three-dimensional morphological images is covered. The images produced may be representations of the value or temporal change in value of a physiological parameter such as temperature, pH, oxygen tension and the like. Morphological images however will generally be produced. For in vivo imaging, the MR imaging agent should of course be physiologically tolerable or be capable of being presented in a physiologically tolerable form.

Particularities of the Invention with Special Respect to the Variant of the Invention Using Para-Hydrogen as the Source of Nuclear Spin Polarization In the following, particularities of the present invention are described with respect to a use of para-hydrogen as the symmetric molecule. However, para-hydrogen should be understood here as an example, and the particularities of the invention listed below can also be applied with other types of symmetric molecules. In the same way, a metal complex should be understood as an example for a site of ordered environment, and other types of templates offering sites of ordered environment may be applied alternatively. The following is to be understood as an alternative and independent approach to describe the invention.

The invention relates to, in particular, a process for producing a compound comprising a hyperpolarized nucleus, which comprises:
  (a) arranging parahydrogen or a hyperpolarized derivative thereof and a compound comprising a hyperpolarizable nucleus in an ordered environment such that hyperpolarization is directly transferable from the parahydrogen or derivative to the hyperpolarizable nucleus;
  (b) directly transferring hyperpolarization from the parahydrogen or derivative to the hyperpolarizable nucleus; and
  (c) separating the compound comprising the hyperpolarized nucleus from the ordered environment and the parahydrogen or derivative thereof.

Said process can provide that the parahydrogen is present in parahydrogen-enriched hydrogen.

Further, said process can provide that the parahydrogen derivative comprises a pair of hydride ligands whose nuclei are hyperpolarized.

Further, said process can provide that the ordered environment comprises a hydrogenated metal complex comprising a pair of hydride ligands whose nuclei are hyperpolarized and a ligand comprising a hyperpolarized nucleus, and wherein the process comprises directly transferring hyperpolarization from the hydride ligands to the hyperpolarizable nucleus and separating the ligand comprising the hyperpolarized nucleus from the complex.

In this variant, the process can provide that the hydrogenated metal complex is formed by reacting parahydrogen with a hydrogenatable metal complex comprising the ligand comprising the hyperpolarizable nucleus.

In the same variant, the process can provide that the hydrogenated metal complex is formed by reacting a ligand comprising the hyperpolarizable nucleus with a metal complex hydrogenated with parahydrogen.

The process can provide that the reaction is conducted in a fluid comprising para-hydrogen.

It can be provided that the fluid comprises parahydrogen-enriched hydrogen. Further, it can be provided that the hydride ligands are in equilibrium with the hydrogen in said solution.

Further, the process can provide that the hydride ligands are in a cis arrangement.

The process can provide that the ligand is attached to the metal via an atom containing said hyperpolarizable nucleus.

The process can also provide that the metal complex is present in a solution comprising said ligand in unbound form.

In the latter case, the process can provide that the bound ligand is labile and in equilibrium with unbound ligand.

The process can provide that the complex is bound to a support. Further, the process can provide that the complex is a transition metal complex.

In the latter case, it can be provided that the complex comprises a transition metal selected from Ru, Rh, Ir, W, Pd and Pt.

Further, the process can provide that process the compound comprising the hyperpolarizable nucleus is a metabolite, a drug or a prodrug.

Further, the process can provide that the hyperpolarizable nucleus is a $^{1}H$, $^{29}Si$, $^{13}C$, $^{15}N$ or $^{31}P$ nucleus.

The process can provide that the hyperpolarization is transferred spontaneously.

The process can also provide that the hyperpolarization is transferred using a pulse sequence.

The invention further relates to, in particular, a device for producing a compound comprising a hyperpolarized nucleus, which comprises a reaction chamber comprising:
  a) an inlet for a fluid enriched with para-hydrogen; and
  b) a metal complex attached to a support, wherein the complex is hydrogenatable or hydrogenated with parahydrogen.

The device may provide that the metal complex is hydrogenated with parahydrogen.

The device may also provide that the metal complex is hydrogenatable with parahydrogen.

Further, the device may provide that the metal complex comprises a ligand which is a compound comprising a hyperpolarizable nucleus.

The device may be further comprising an inlet for a solution comprising a ligand in unbound form, wherein the ligand is a compound comprising a hyperpolarizable nucleus.

The device may be further comprising an outlet for one or more fluids.

The invention further relates to, in particular, a compound comprising at least one hyperpolarized nucleus, obtainable by a process as mentioned above.

The compound may be a metabolite.

The compound may provide that the hyperpolarized nucleus is a heteroatomic nucleus.

The compound may be for use in diagnosis or therapy.

The invention further relates to, in particular, a use of a compound as mentioned above as a magnetic resonance (MR) contrast agent.

The invention further relates to a composition comprising a compound as mentioned above and a physiologically acceptable carrier or excipient.

The invention further relates to, in particular, a hydrogenated metal complex comprising a pair of hydride ligands whose nuclei are hyperpolarized and a ligand comprising a hyperpolarizable nucleus, wherein the hydride ligands are arranged such hyperpolarization can be directly transferred to the hyperpolarizable nucleus.

The complex may prove that the ligand is a labile ligand.

The complex may further provide that the ligand is a metabolite.

The complex may further provide that the hyperpolarized nucleus is a heteroatomic nucleus.

The complex may be attached to a solid support.

We claim:

1. A method for carrying out an NMR experiment with enhanced sensitivity on a compound comprising hyperpolarizable nuclei, the method comprising the steps of:
    a) preparing a fluid having a temperature TF, containing spatially symmetric molecules comprising two halves each, with a non-Boltzmann nuclear spin state distribution of the symmetric molecules at this temperature TF;
    b) providing a compound with a defined chemical identity;
    c) providing a template that offers sites of ordered environment for the two halves of a symmetric molecule and a compound which can be arranged at each site, wherein the ordered environment distinguishes chemically or magnetically the two halves of a symmetric molecule arranged at each site, wherein the ordered environment allows interaction via scalar coupling or dipolar coupling between the two halves of a symmetric molecule and a compound arranged at each site;
    d) bringing together the prepared fluid, the provided compound and the provided template, thereby transferring the spin order from the symmetric molecules to the hyperpolarizable nuclei of the compound during a temporary association of the symmetric molecules, the compound, and the template while ultimately keeping the chemical identity of the compound; and
    e) performing an NMR measurement on the compound comprising hyperpolarized nuclei prepared in step d).

2. The method of claim 1, wherein the symmetric molecules comprise para-hydrogen.

3. The method of claim 1, wherein the sites of ordered environment each comprise a metal complex or a transition metal complex.

4. The method of claim 1, wherein the template comprises a zeolite.

5. The method of claim 1, wherein the hyperpolarizable nuclei of the compound include H, D, $^{29}$Si, $^{13}$C, $^{15}$N, $^{31}$P and/or $^{19}$F.

6. The method of claim 1, wherein the compound is a metabolite.

7. The method of claim 1, wherein, for attaching to a site of ordered environment, the compound comprises an electron donor, N, NH, S, P or O.

8. The method of claim 1, wherein the compound is a gas or ($^{13}$C)O$_2$.

9. The method of claim 1, wherein, at the end of step d), the compound comprising hyperpolarized nuclei is separated from the site of ordered environment.

10. The method of claim 1, wherein, in step d), the spin order is transferred spontaneously.

11. The method of claim 1, wherein, during step d), the entirety of the prepared fluid, the provided compound and the provided template brought together is shaken.

12. The method according to claim 11, wherein, during shaking, the entirety is exposed to a magnetic field, a magnetic field of field strength 1 T, or less or a magnetic field of field strength between 20 µT and 0.1 T.

13. The method of claim 1, wherein, during step d), the entirety of the prepared fluid, the provided compound and the provided template brought together is exposed to an oscillating magnetic field or to an oscillating magnetic field having a field strength between 20 µT and 0.1 T.

14. The method of claim 1, wherein the chemical identity of the compound as prepared in step b) is the same as the chemical identity of the compound as subject to the NMR measurement of step e).

15. Use of the method of claim 1 in an NMR imaging experiment or in an NMR imaging experiment in which the compound is used as a contrast agent.

* * * * *